United States Patent
Abendschein (10) Patent No.: US 8,226,726 B2
(45) Date of Patent: Jul. 24, 2012

(54) METHOD AND INSTRUMENTATION FOR PATELLO-FEMORAL JOINT REPLACEMENT

(75) Inventor: Walter F. Abendschein, Middleburg, VA (US)

(73) Assignee: Biomet Manufacturing Corp., Warsaw, IN (US)

( * ) Notice: Subject to any disclaimer, the term of this patent is extended or adjusted under 35 U.S.C. 154(b) by 336 days.

(21) Appl. No.: 12/553,187

(22) Filed: Sep. 3, 2009

(65) Prior Publication Data

US 2009/0326660 A1    Dec. 31, 2009

Related U.S. Application Data

(63) Continuation of application No. 10/366,415, filed on Feb. 14, 2003, now abandoned.

(60) Provisional application No. 60/356,876, filed on Feb. 14, 2002.

(51) Int. Cl.
*A61F 2/38* (2006.01)

(52) U.S. Cl. .................................................. 623/20.14

(58) Field of Classification Search .... 623/20.14–20.19, 623/20.21, 20.35, 20.36, 23.23, 23.28, 23.29, 623/23.3, 23.5, 23.55
See application file for complete search history.

(56) References Cited

U.S. PATENT DOCUMENTS

| | | | |
|---|---|---|---|
| 3,506,982 A | 4/1970 | Steffee | |
| 3,656,186 A | 4/1972 | Dee | |
| 3,694,821 A | 10/1972 | Moritz | |
| 3,760,427 A | 9/1973 | Schultz | |
| 3,774,244 A | 11/1973 | Walker | |
| 3,806,961 A | 4/1974 | Muller et al. | |
| 3,878,566 A | 4/1975 | Bechtol | |
| 4,007,495 A | 2/1977 | Frazier | |
| 4,052,753 A | 10/1977 | Dedo | |
| 4,085,466 A | 4/1978 | Goodfellow et al. | |
| 4,151,615 A | 5/1979 | Hall | |
| 4,285,070 A | 8/1981 | Averill | |
| D272,648 S | 2/1984 | Bolesky et al. | |
| 4,944,756 A | 7/1990 | Kenna | |
| 4,979,957 A | 12/1990 | Hodorek | |
| 5,024,670 A | 6/1991 | Smith et al. | |
| 5,176,684 A | 1/1993 | Ferrante et al. | |
| 5,181,924 A | 1/1993 | Gschwend et al. | |
| 5,246,460 A | 9/1993 | Goodfellow et al. | |

(Continued)

FOREIGN PATENT DOCUMENTS

JP     50155092     12/1975

(Continued)

OTHER PUBLICATIONS

Goodfellow, John. D. et al.; Patello-Femoral Joint Mechanics and Pathology,The Journal of Bone and Joint Surgery, vol. 58-B, No. 3, pp. 287-290, Aug. 1976.

(Continued)

*Primary Examiner* — Eduardo C Robert
*Assistant Examiner* — David Comstock
(74) *Attorney, Agent, or Firm* — Harness, Dickey (57) ABSTRACT

A patello-femoral joint prosthesis is provided which allows smooth tracking of the articulating surfaces through a full range of joint motion. A novel configuration of a femoral implant component that facilitates superior adhesion to bone is also provided. Also provided is a patello-femoral joint replacement system, which permits precise, reproducible bone preparation techniques that uniquely permit later revision and full knee joint replacement procedures with minimal complications. Also provided are a drill guide and a cutting guide, each being configured to provide three point stabilization during operation.

21 Claims, 12 Drawing Sheets

U.S. PATENT DOCUMENTS

| | | | |
|---|---|---|---|
| 5,314,480 | A | 5/1994 | Elloy et al. |
| 5,358,529 | A | 10/1994 | Davidson |
| 5,397,360 | A | 3/1995 | Cohen et al. |
| 5,556,433 | A | 9/1996 | Gabriel et al. |
| 5,571,196 | A | 11/1996 | Stein |
| 5,601,550 | A | 2/1997 | Esser |
| 5,609,644 | A | 3/1997 | Ashby et al. |
| 5,720,752 | A | 2/1998 | Elliott et al. |
| 5,824,098 | A | 10/1998 | Stein |
| 2002/0029045 | A1 | 3/2002 | Bonutti |
| 2003/0181984 | A1 | 9/2003 | Abendschein |

FOREIGN PATENT DOCUMENTS

| | | |
|---|---|---|
| JP | 572823 | 10/1993 |
| JP | 6296630 | 10/1994 |
| JP | 8238265 | 9/1996 |
| JP | 2002035020 | 2/2002 |

OTHER PUBLICATIONS

Harwin, Steven F.; Patellofemoral Complications in Symmetrical Total Knee Arthroplasty; The Journal of Arthroplasty, vol. 13, No. 7, pp. 753-762, Oct. 1998.

Kober, Scott; "Indications Expanding for Patellofemoral Prosthesis" Orthopedics Today (p. 22).

Ackroyd C.E., Newman J.H.; The Avon Patello-Femoral Arthroplasty-Development and Early Results; The Journal of Bone and Joint Surgery [BR] 2001; vol. 83-B; Supplement II.

Back, D.L. et al.; The Kinemax Total Knee Arthroplasty, The Journal of Bone and Joint Surgery, vol. 83-B, No. 3, pp. 359-363, Apr. 2000.

CE Ackroyd, J.H. Newman; The Avon Patello-Femoral Arthoroplasty: Two to Five Year Results; J.Bone Joint Surg [Br] 2003; vol. 85-B; Supplement II; British Orthopaedic Association (pp. 161-163).

METHOD AND INSTRUMENTATION FOR PATELLO-FEMORAL JOINT REPLACEMENT

CROSS-REFERENCE TO RELATED APPLICATIONS

This application is a continuation application of U.S. patent application Ser. No. 10/366,415 filed on Feb. 14, 2003, which claims the benefit of U.S. Provisional Application No. 60/356,876, filed on Feb. 14, 2002. The entire disclosure of each of the above applications is incorporated herein by reference.

FIELD

This invention relates generally to novel orthopedic joint replacement implants and methods, and particularly to an improved method and system for patello-femoral joint replacement through a simpler, less invasive surgical approach with instrumented, reproducible cuts.

BACKGROUND

Patello-femoral joint replacement is a well known orthopedic surgical procedure. A variety of conventional joint replacement devices have been in use since the 1970's, however, unlike joint prostheses, which are typically used in total knee replacement surgery, conventional patello-femoral joint replacement devices have not been widely accepted in the orthopedic community. This may be due to the somewhat mixed clinical results that conventional patello-femoral joint prostheses have demonstrated as presented in the pertinent medical literature. The conventional prostheses typically include femoral components that were larger, bulkier devices contoured to fit the trochlear groove of the femur. Their contoured geometry, however, made it almost impossible to develop a precise method of preparing the diseased surface of the femur to fit the geometry of the implant. Typically the surgeon when using conventional patello-femoral joint replacement devices has to use powered burrs to carve out the boney surface to accept the implant. This makes the fit and alignment of the implants hard to reproduce, and somewhat variable from case to case. This method, and the large size of the implants, also led to difficulties, if and when, it may be necessary to revise the implant. It is not uncommon for it to be necessary to revise the implants to total knee replacements in later years as the arthritis progresses. For this reason the ability to easily perform a revision procedure without excess sacrifice of bone is crucial.

The use of precise cutting guides for other knee replacement procedures slowly came into practice in orthopedics in the early 1980's. Similar improvements in the devices and methods used in patello-femoral joint replacement have not been seen. Prior to the present invention, there have not been methods or surgical devices that permit accurate, reproducible bone cuts in the replacement of the patello-femoral joint.

Early attempts to improve the devices used in patello-femoral joint replacement include those described in U.S. Pat. Nos. 4,007,495 and 4,151,615. Both of these early patents describe patello-femoral joint replacements, but they do not address the method, or instrumentation required to implant the products. Similarly, U.S. Pat. No. 3,878,566, which describes a commercially successful patello-femoral joint device, provides no improvement in the method of implanting the device as it simply discloses that the prosthesis is implanted by simply burring out a spot for it in the bone. There is no disclosure of a means or method for aligning or guiding the surgeon's preparation of the bone for improved implantation of the device. U.S. Pat. No. 5,609,644 includes claims, which are drawn to a patello-femoral joint, however, only the patellar replacement component is described in any detail and no device or method is disclosed that would assist the surgeon in the accurate implantation of the device.

U.S. Pat. Nos. 5,571,196 and 5,824,098, both issued to Stein, attempt to address this need by describing a system of instrumentation that includes an intramedullary guide rod and a router frame for preparing a trough in the anterior femur. The system disclosed by Stein does not retain the anatomical contour of the femur and requires several additional steps in the operation thereby making the process more complicated and more prone to complications. The method of Stein is also far more invasive that the present invention, and, unlike the present invention, once implanted would not allow an uncomplicated revision, if necessary, since the machined femoral trough taught by Stein is much more bone sacrificing and is not aligned with standard total knee geometries.

These prior art attempts to provide a patello-femoral joint replacement system have all failed to incorporate a low profile femoral implant design with geometrically defined angular surfaces similar to those in the femoral components of total knee replacements, combined with a series of simple precise cutting guides, that provide accurate, reproducible cuts.

In response to this need the present invention described herein has been developed.

SUMMARY

It is the general object of the present invention to provide a novel patello-femoral joint replacement system and method for use thereof, that after implantation allows essentially normal, full range motion of the prosthetic joint.

It is a further object of this invention to provide a smaller, lower profile, femoral implant than conventional implants with a flat anterior bone-facing surface providing improved adhesion between the anterior surface of the femur and the femoral implant, angling slightly superiorly to facilitate full range of motion of the joint, said bone-facing surface incorporating a roughened texture, recessed pockets, and undercut edges on the bone-facing surface for enhanced fixation and retention of bone cement; a concave articular surface which mates with the articular surface of the patellar component; and an intramedullary stem for alignment in the femoral canal.

It is still further an object of this invention to provide a system of surgical instruments comprising an intramedullary guide rod; an anterior femoral cutting guide, which adapts to, and is based on the intramedullary guide rod; a guide for drilling with precision the intramedullary canal of the femur, which has means for aligning and positioning it relative to the anterior surface of the femur; a conically shaped rasp or file for finishing the anterior cut and preparing it for receiving the femoral implant; a feeler gauge for accurately positioning the cutting guide; and an impactor, as is commonly known in the art, for facilitating the final seating of the femoral implant.

It is further an object of the present invention to provide the system of surgical instruments described immediately above as a kit, which can be provided with instructions for use, bone adhesive, alternative embodiments or sizes of member components so as to allow the surgeon to modify the system to fit the immediate needs of the patient.

It is still further an object of this invention to provide a femoral implant, which is the femoral resurfacing component of the present invention, the implant requiring only one cutting step for the bone to be prepared for implantation, incorporating a geometry that facilitates later revision to a total knee, if necessary, and articulating with a patellar component that incorporates a mating, reciprocal, articular surface.

It is further an object of the present invention to provide a method for patello-femoral joint replacement that includes the process of making a smaller less invasive incision in the patient; drilling with precision an intramedullary guide hole in the femur; aligning a novel cutting guide to an intramedullary rod inserted in the guide hole; making a single, precise cut on the anterior surface of the femur; and implanting the femoral resurfacing component of the system of the present invention.

DRAWINGS

The exact nature of this invention, as well as its objects and advantages, will become readily apparent upon reference to the following detailed description when considered in conjunction with the accompanying drawings, in which like reference numerals designate like parts throughout the figures thereof and wherein.

DETAILED DESCRIPTION

The present invention provides a system, including a patello-femoral joint replacement device, a series of instruments, and a method of use of those instruments for implanting the patello-femoral joint replacement device.

Figure 1A:
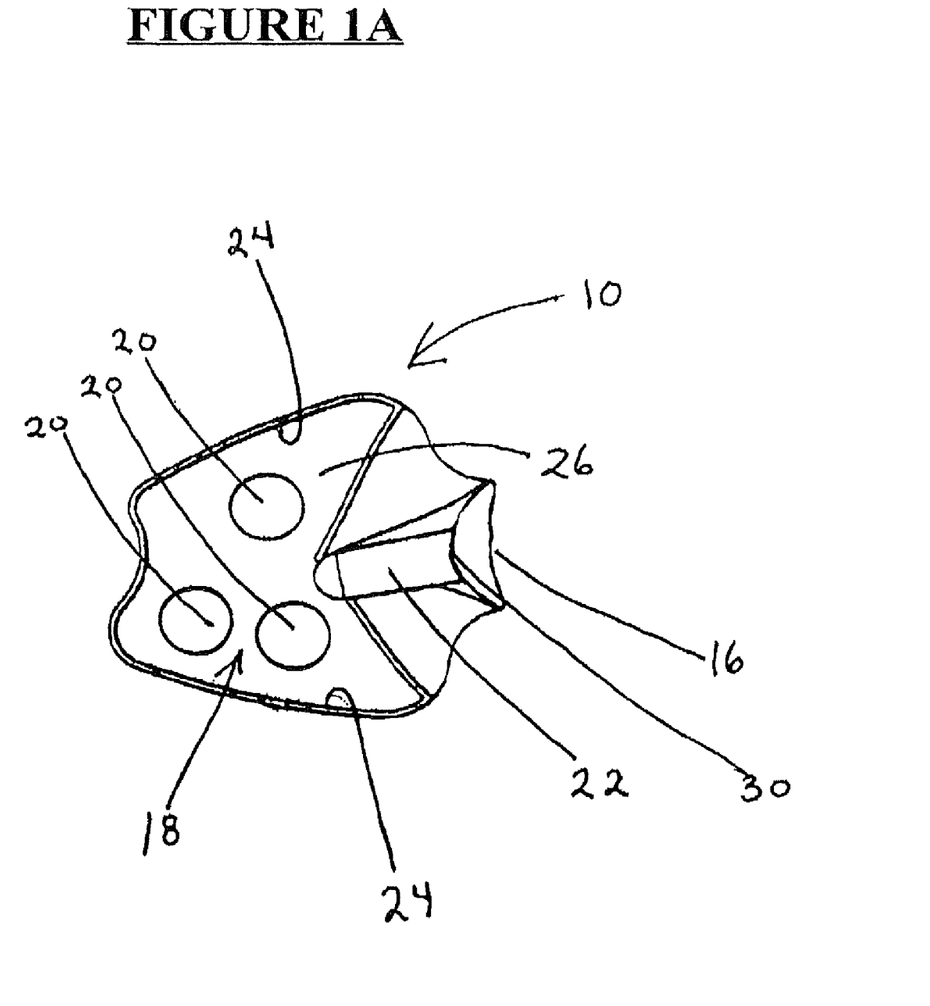
FIGS. 1A, 1B, 1C show a front, side and back view respectively of one embodiment of the femoral implant component of the present invention.
Figure 1B:
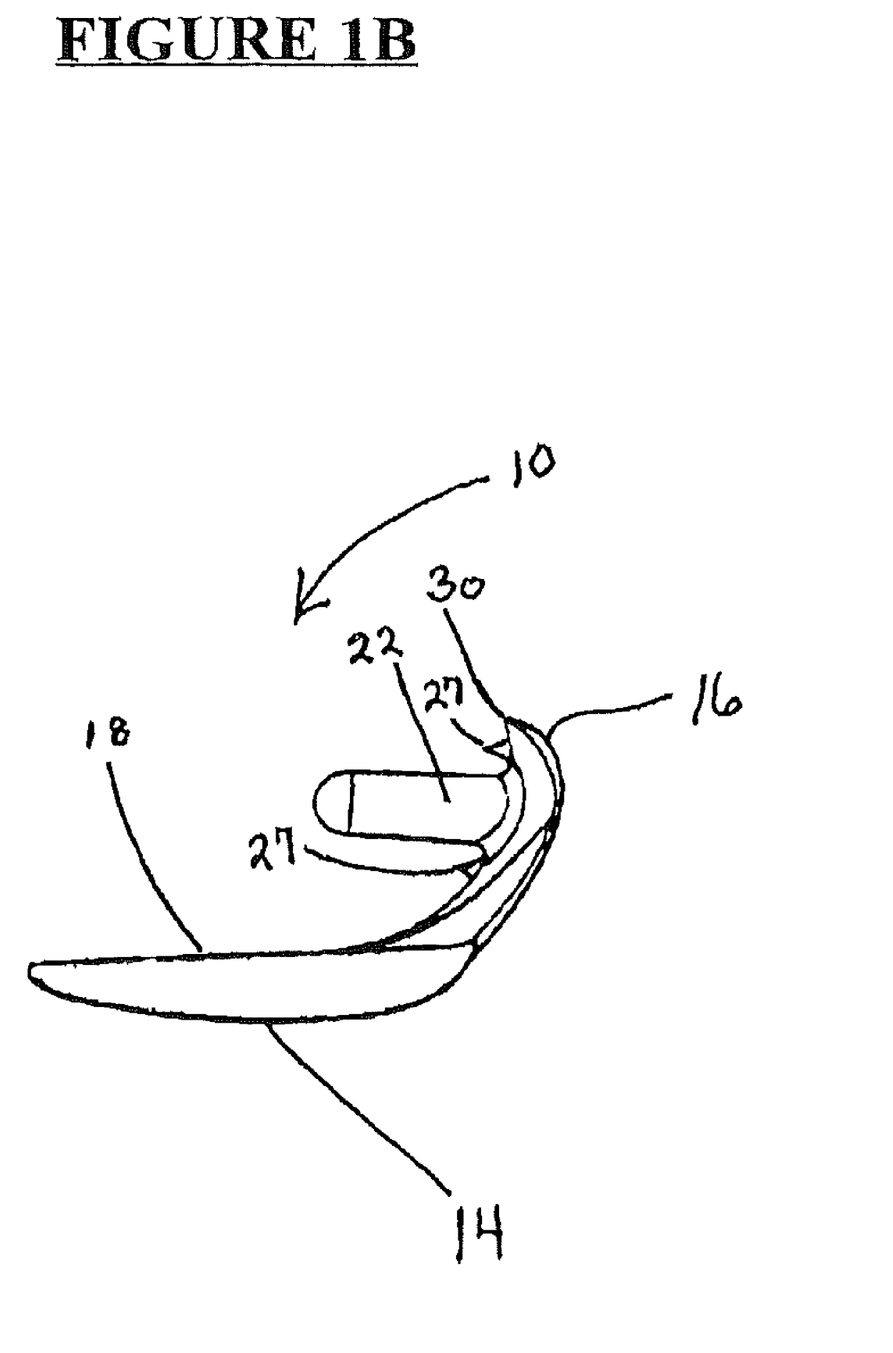
Figure 1C:
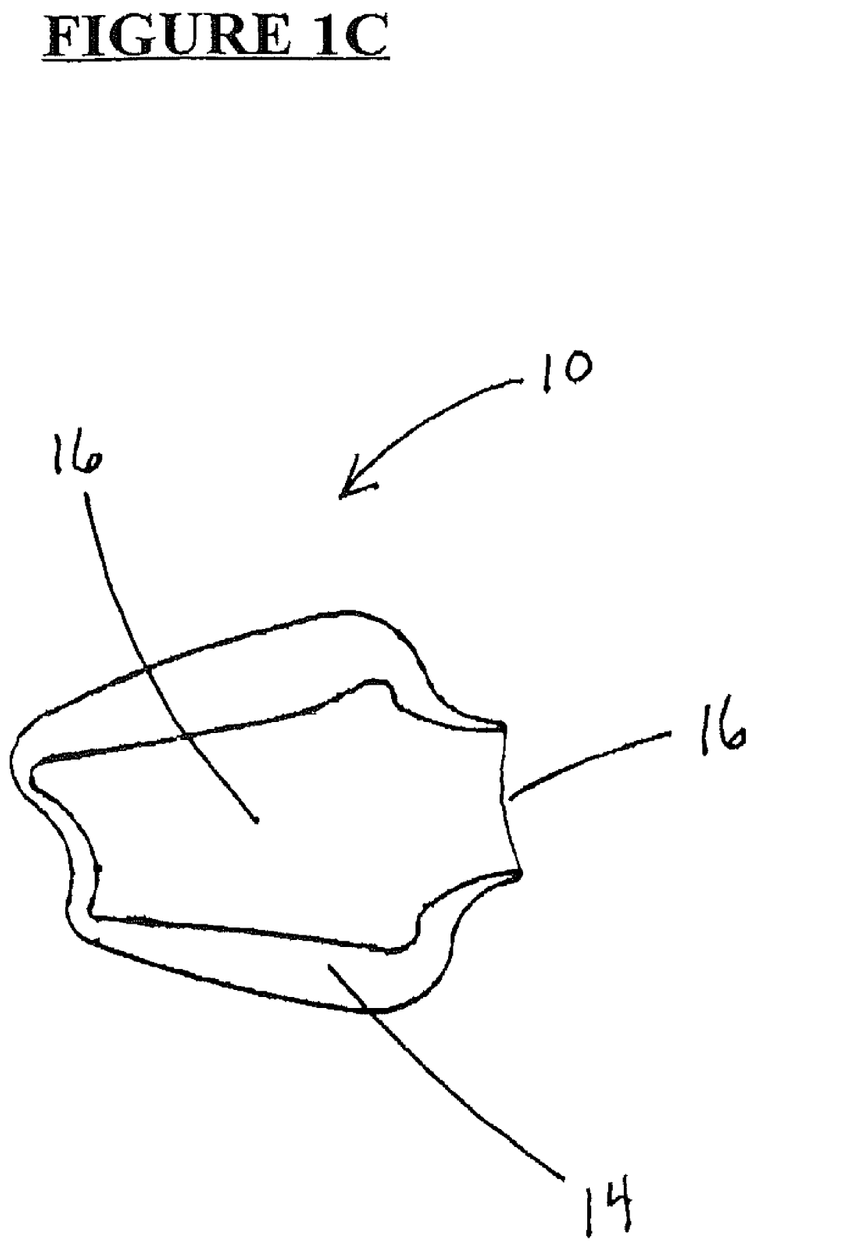
Figure 2A:
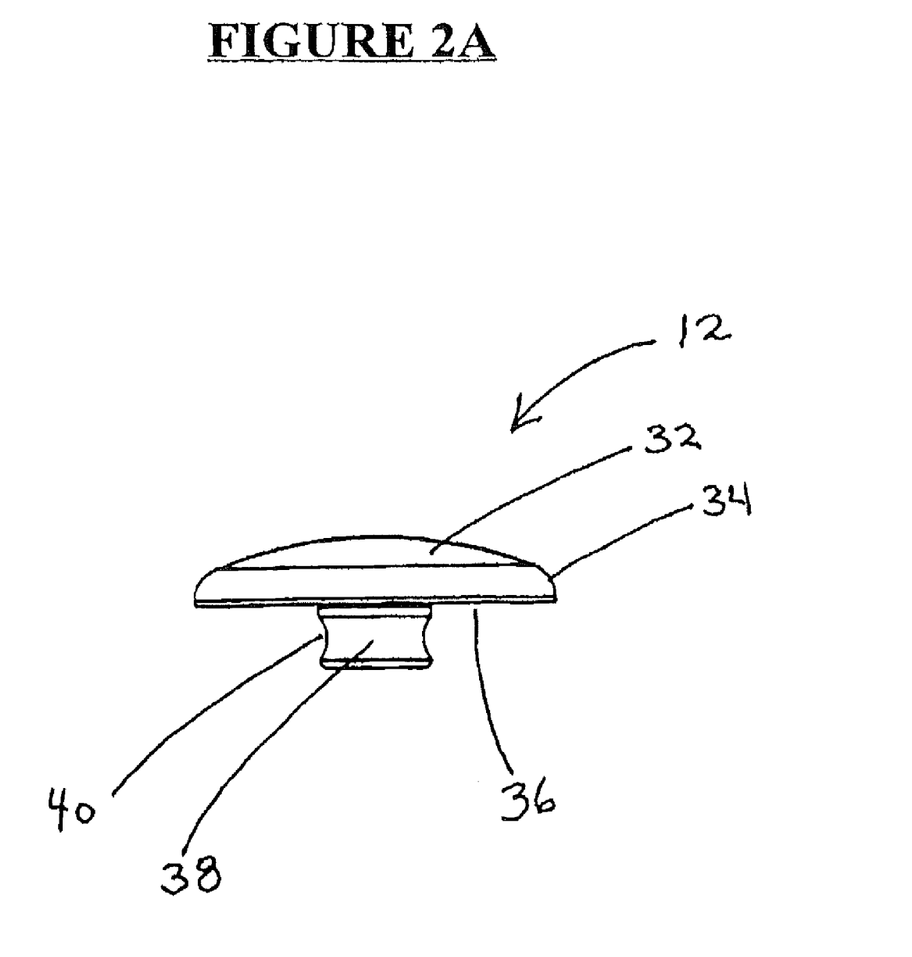
FIGS. 2A, 2B show a front and side view of one embodiment of the patellar implant component of the present invention.
Figure 2B:
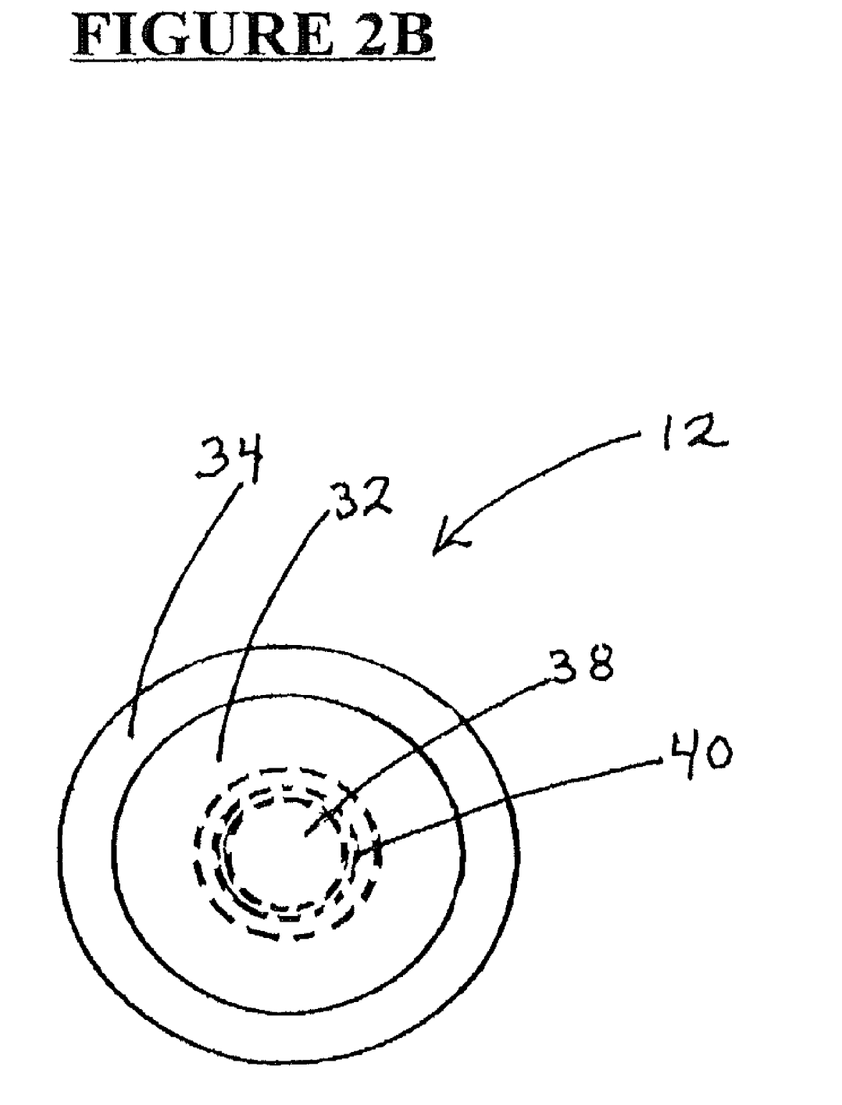

The patello-femoral joint replacement device is made up generally of two articulating components, a femoral implant, best demonstrated in FIGS. 1A-C and generally shown at (10) and a patellar implant, best demonstrated in FIGS. 2A-B and generally shown at (12).

As best shown in FIGS. 1A-C, the femoral implant (10) is designed to replace the anterior surface of the distal portion of the patient's femur. The femoral implant (10) includes an anatomically shaped upper surface (14) with a centrally and longitudinally oriented articulating groove (16) of a generally concave configuration.

As best shown in FIG. 1A, the underside (18) of the femoral implant (10) includes at least one, but preferably multiple recessed pockets (20), at least one intramedullary stem (22), and a circumferentially disposed undercut edge (24). At least a portion and preferably the majority of the underside generally shown at (18) of the femoral implant (10) is provided with a roughened surface (26). A porous coating or the use of at least one, preferably multiple spikes or pegs (27) to improve attachment and adhesion can also be employed. The recessed pockets (20), undercut edge (24), and the roughened surface (26) individually and together provide a configuration that facilitates a firm and lasting connection of an adhesive that serves to bond the underside (18) of the femoral implant (10) to the prepared anterior surface of the distal portion of the femur.

It is within the concept of the present invention to employ any adhesive in the practice of the method of implanting the present invention in a patient. Preferably a bone cement will be employed.

As best shown in FIGS. 1A,B, the articulating groove (16) continues without interruption from the upper surface (14) to distally extending projection (28) that terminates angling slightly superiorly at an articulating groove distal terminus (30). This distal terminus (30), by presenting a slightly superior angle enables the patello-femoral joint replacement device to have smooth tracking of the patellar implant (12) in the articulating groove (16) through the full range of motion of the joint, that is in extremes of flexion.

The patellar implant (12), as best shown in FIGS. 2A,B, includes an articulating surface (32) having a generally spherical dome-shaped geometry and being sized and configured to slidably articulate in a complementary fashion within the articulating groove (16) of the femoral implant (10). The articulating surface (32) can include a circumferentially disposed annular border (34) having a slightly different geometry than that of the articulating surface (32) and composed of different materials than that of the articulating surface (32).

A securing surface (36) disposed on the opposite side of the patellar articulating surface (32) is configured to facilitate secure attachment to bone and can include a patellar roughened surface (38) to facilitate bonding of an adhesive. The securing surface also includes at least one bone anchor (40) that can be configured to include an annular retaining groove (42). The patellar roughened surface (38), the bone anchor (40), and the annular retaining groove (42) independently and collectively serve to facilitate a strong adhesive bond between the patellar implant (12) and bone material. It is within the concept of the present invention that the patellar implant (12) can have additional pegs on the securing surface (36) to facilitate strong adhesion to the bone.

The system of the present invention includes several instruments which provide the using surgeon with the ability to precisely drill and cut bone material of the distal portion of the femur in such a way as to provide contact with the femoral implant (10) that is far superior to conventional bone preparation methods.

Figure 3:
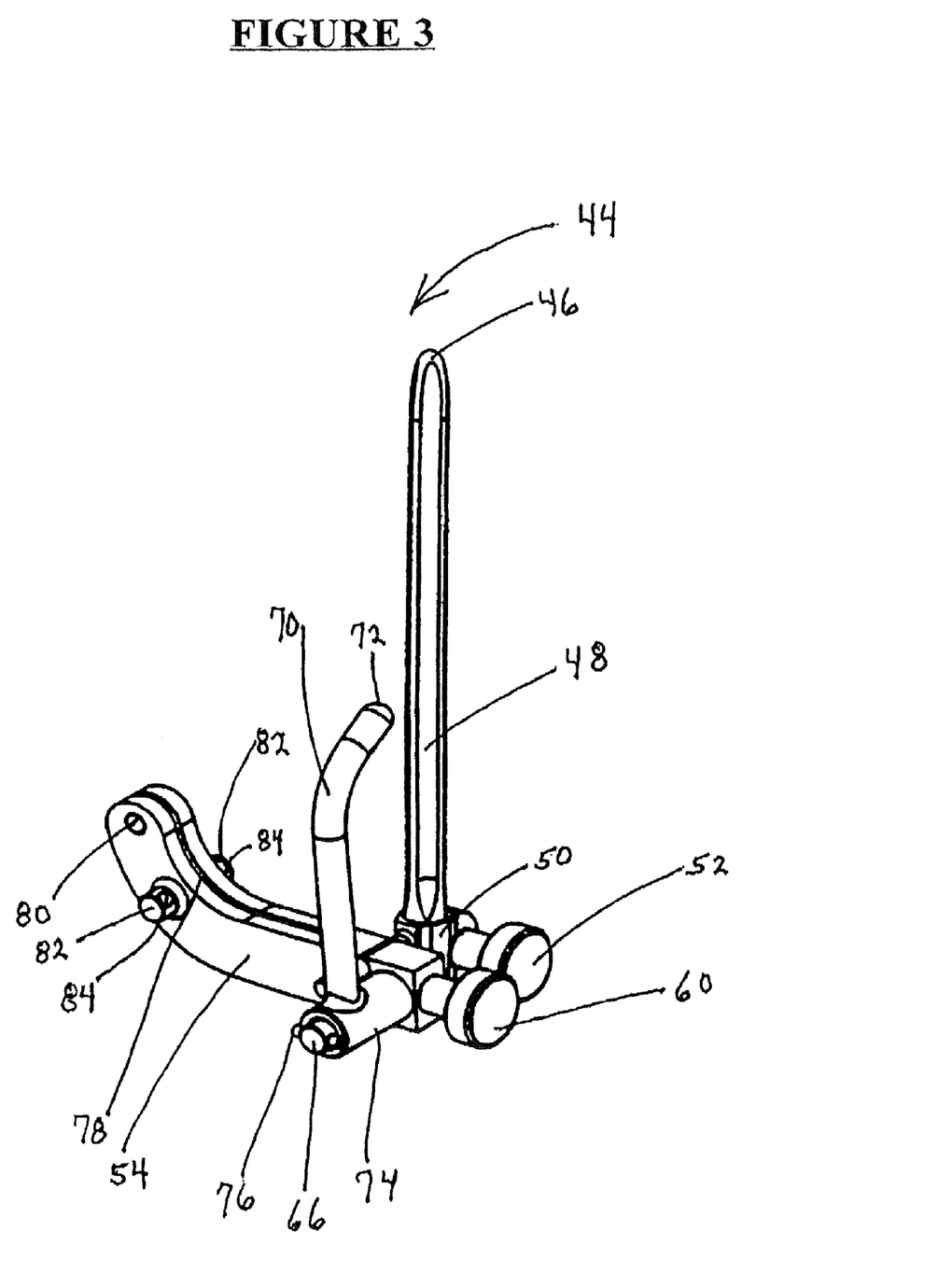
FIG. 3 shows an isometric view of one embodiment of the cutting guide component of the present invention.
Figure 4:
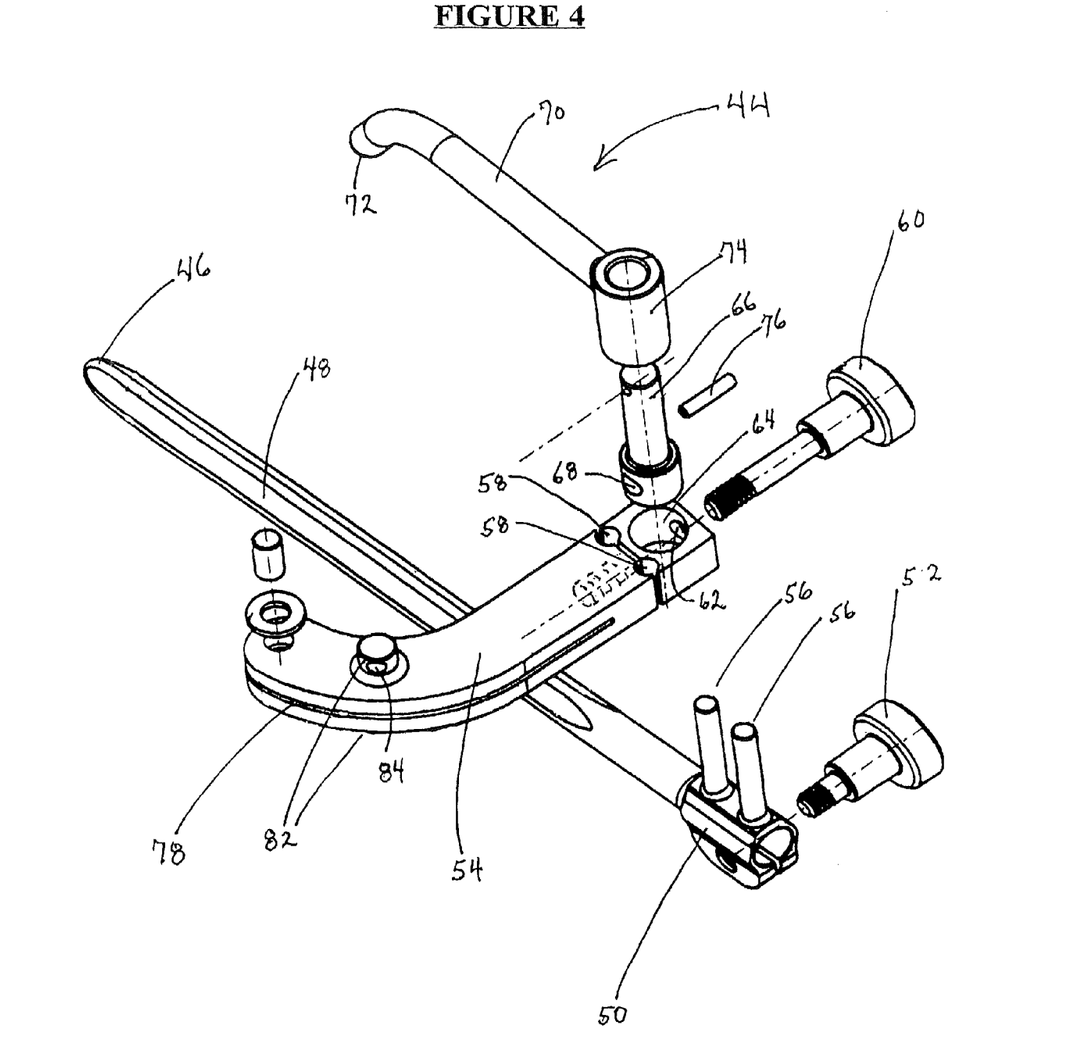
FIG. 4 shows an exploded view of the embodiment of the cutting guide component of the present invention shown in FIG. 3.
Figure 5:
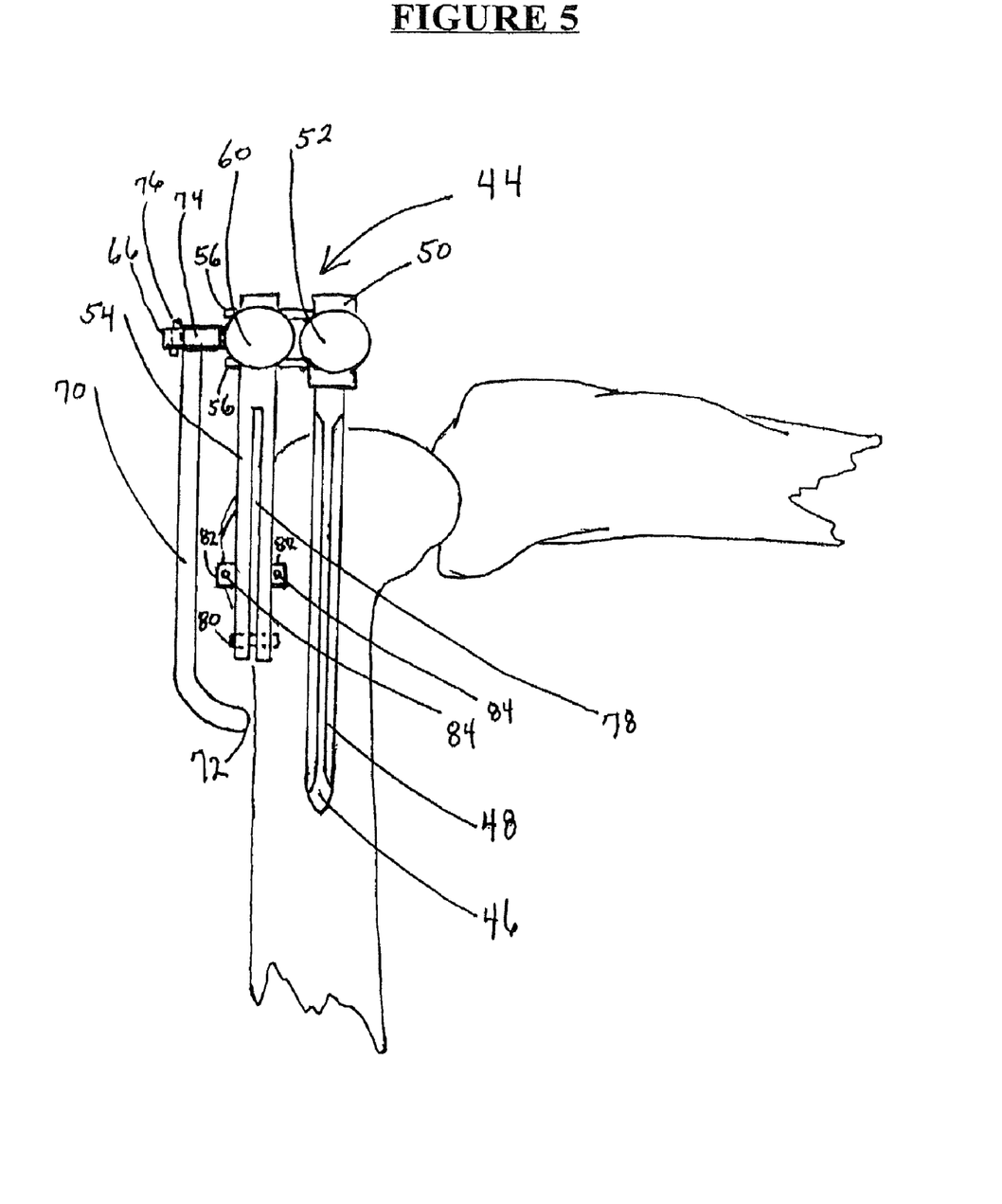
FIG. 5 shows the cutting guide component of the present invention shown in FIGS. 3 and 4 operationally disposed in contact with the distal end of a femur.

As best seen in FIGS. 3-5, the present invention provides a bone cutting guide, generally shown at 44, that includes an intramedullary rod (46) sized and configured for insertion into the intramedullary space of a femur that has been prepared to receive the same. The intramedullary rod (46) can be configured with one or more groves (48) so as to provide a fluted surface along the longitudinal axis of the intramedullary rod (46). This fluted surface can facilitate insertion of the intramedullary rod (46) into the bone so as to reduce the pressure imposed on the marrow of the bone and thus reduce or avoid the pressure-induced result of material being forced into the circulation system of the patient. In a preferred embodiment of the present invention, the intramedullary rod (46) is fixedly connected to cutting guide (44). It is, however, entirely within the scope of the invention to configure the intramedullary rod (46) to be releasably engaged to the cutting guide (44) by a rod gripping member (50) that can be selectively secured by means of a gripping member actuator (52). Such an alternative embodiment of the cutting guide (44) can permit removal and replacement of the intramedullary rod (46) with rods of different configuration or different size.

Whether integrally formed with the intramedullary rod (46), as in the preferred embodiment, or connect thereto by an intermediary member, such as the gripping member (50), the intramedullary rod (46) is releasably connected to a saw guide member by at least one, preferably two cutting guide assembly rods (56), which are sized and configured to slidably engage a like number of assembly rod receiving portals (58). An assembly securing member (60) is configured to releasably engage a securing member portal (62) in such a manner so as to cause the receiving portal (58) to secure the assembly rods (56) to the saw guide member (54).

The saw guide member (54) is provided with a anchor portal (64) that is sized and configured to receive a stylus arm anchor rod (66). The stylus arm anchor rod (66) can be integrally connected to the saw guide member (54) or preferably can be releasably secured into the anchor portal (64) by passage of the assembly securing member (60) through an anchor rod passage (68).

A freely rotating stylus (70) is sized and configured to provide at a distal end a stylus-femoral contact point (72). The proximal end of the stylus (70) is attached at approximately a right angle to a stylus rotation sleeve (74), which is sized and configured to be circumferentially disposed and freely rotate around the stylus arm anchor rod (66). A stylus retainer member (76) can be provided to releasably retain the stylus (70) in its rotatable configuration around the stylus arm anchor rod (66).

The saw guide member (54) is preferably partially bifurcated by a saw guide slot (78) sized and configured to allow slidable passage of a bone saw such as is commonly known in the art. The distal end of the bifurcated portion of the saw guide member (54) includes a guide connecting member (80) that can be a permanent connection at or near the terminus of the saw guide member (54) or can be a pin, screw, rivet, or any other connecting means that serves to attach the ends of the bifurcated saw guide member (54). Disposed on the outer surface of the bifurcated saw guide member (54) is at least one, preferably two, anchor guides (82), which individually define anchor guide portals (84). These anchor guide portals are sized and configured to facilitate passage of a drill bit that can be used by a surgeon to bore an anchoring hole, such as an intramedullary canal, into the bone of a patient. Upon removal of the drill bit from the anchor guide portals (84), the surgeon can employ the anchor guide portals (84) as securing points through which securing bone screws or the like can be passed to provide additional attachment points for the cutting guide to the bone of the patient during operation. Thus, the surgeon can employ the stylus femoral contact point (72), and the two anchor guide portals (84) to provide three separate securing points for the cutting guide member to the bone. By this means, the surgeon can ensure a stable and well-positioned cutting guide is in place prior to employing a bone saw through the saw guide slot (78).

Figure 6A:
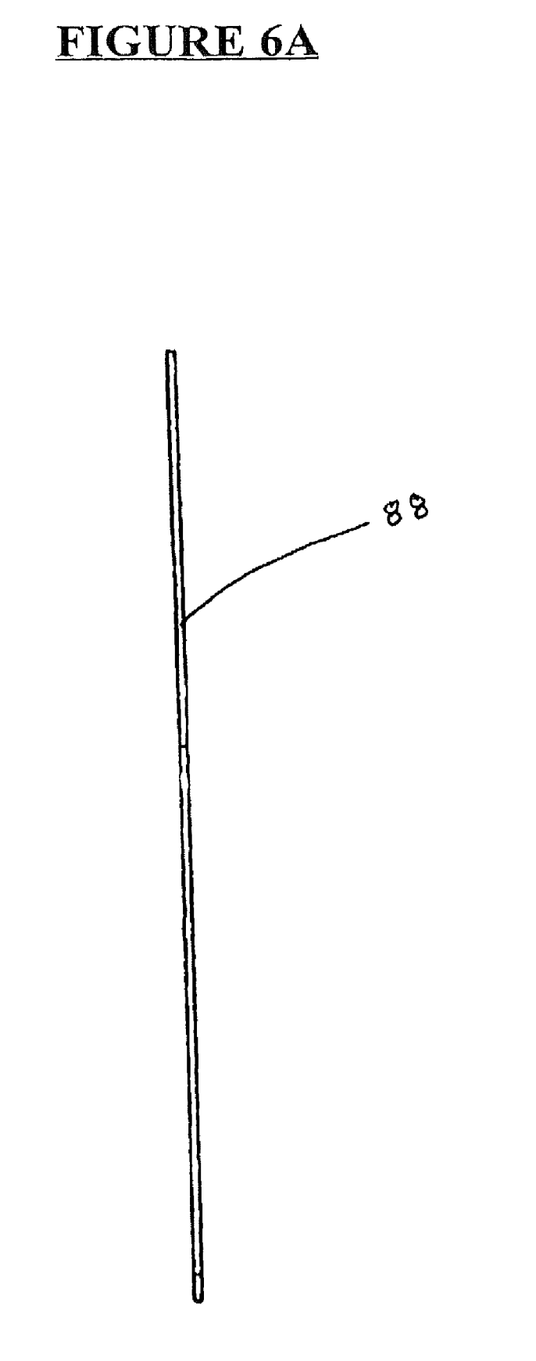
FIGS. 6A, 6B show a plan and side view of one embodiment of the feeler gauge component of the present invention.
Figure 6B:
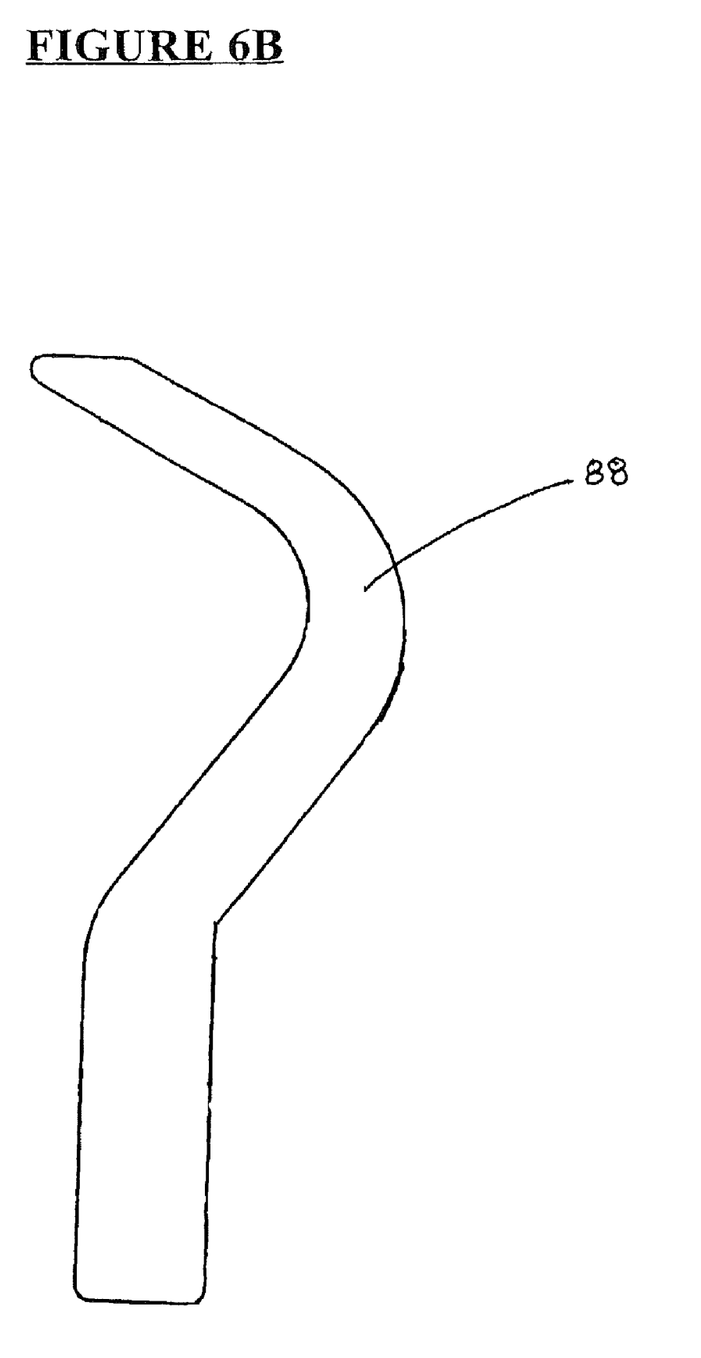

A feeler gauge (88) as is well known in the art and as shown in FIGS. 6A,B can be sized and configured to align the saw guide slot (78) in the cutting guide (44) with the targeted location on the femur.

Figure 7:
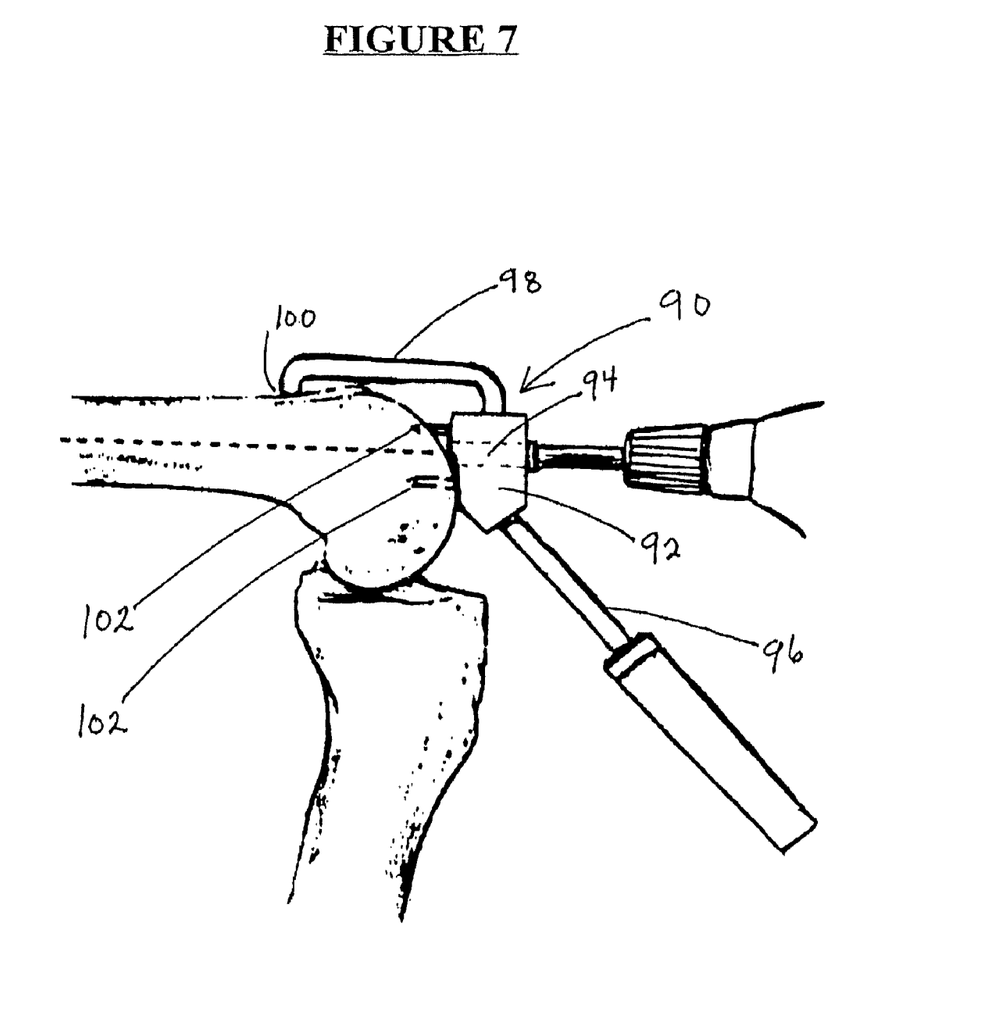
FIG. 7 shows a side view of the drill guide component of the present invention in place against the distal end of a femur for drilling the intramedullary canal.

The system of the present invention can also include a drill guide, as seen in FIG. 7 and generally shown at (90). The drill guide (90) includes a drill guide block (92) that defines a drill guide passage (94). The drill guide block (92) is connected to a drill guide handle (96) by which the surgeon can manipulate and steady the drill guide (90) during operation. A drill guide stylus (98) can be provided as attached to the drill guide block (92) at a proximal end and terminating at a drill guide stylus-femoral contact point (100) at a distal end. The drill guide block can be provided with at least one, preferably two drill guide securing points (102) by which the using surgeon can obtain additional stability of the drill guide (90) during operation. The drill guide (90) of the present invention can be provided with three stabilizing points during operation: the drill guide stylus and the two drill guide securing points. Once positioned and secured, the drill guide (90) can be employed by the surgeon to facilitate the proper alignment and accurate drilling of the intramedullary canal. Once properly drilled, the cutting guide (44) of the present invention can be inserted and accurately positioned for use.

Figure 8:
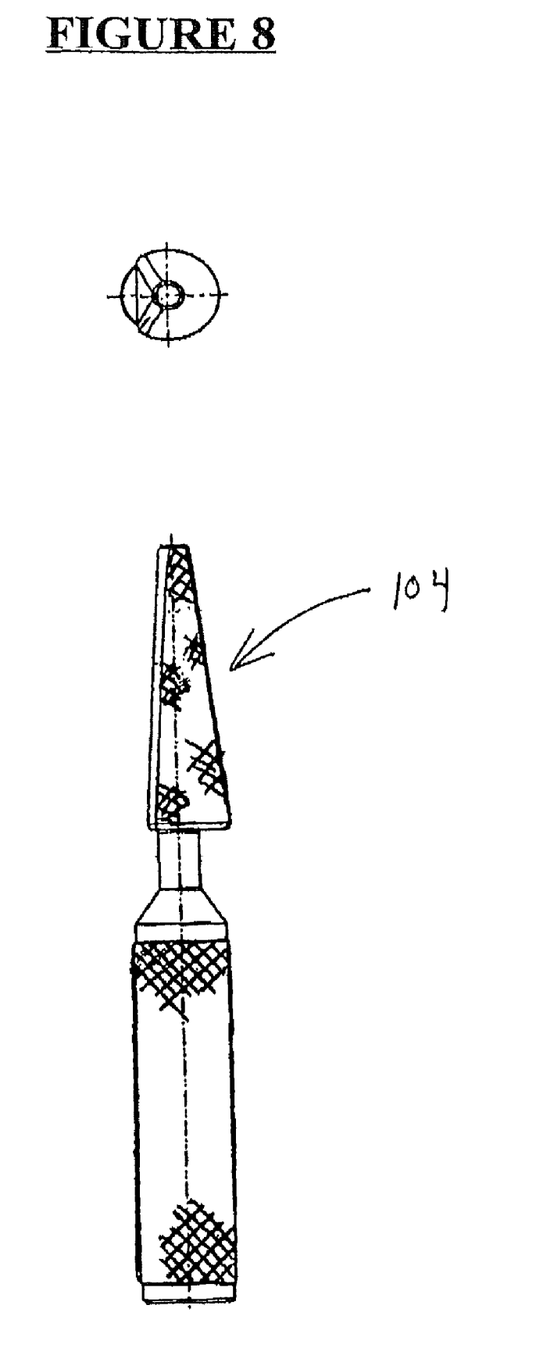
FIG. 8 shows a prospective view of the distal portion of one embodiment of the bone rasp component of the present invention.

The system of the present invention can also include a bone rasp (104). The bone rasp (104) can be conically shaped and at least a portion of the conical terminus can be provided with an abrasive surface as is well known in the art. The bone rasp (104) is configured to facilitate the removal of any burrs, osteophytes or remaining projections of bone after the cutting step of the method of the present invention.

In the method of the present invention, each of the components described above are used as indicated to systematically prepare the femur for receiving the patello-femoral joint replacement device described herein. The drill guide (90) after being properly positioned and used by the surgeon to facilitate the drilling of the femur and the formation of a receiving point for the intramedullary rod (46) is removed. The cutting guide (44) of the system of the present invention is then positioned with the aid of the feeler gauge (88) as described above and used by the surgeon to facilitate a accurate cutting of the bone to remove the anterior surface of the distal end of the femur thus providing a substantially flat receiving surface on the bone. After removal of the cutting guide (44) the femoral implant (10) is positioned and fixedly attached to the anterior surface of the femur wherein the intramedullary stem (22) of the femoral implant (10) is now positioned in the hole earlier drilled by the surgeon and earlier used to assist in the securing of the cutting guide (44). The patellar implant (12) is then implanted by the surgeon and placed in articulating engagement with the femoral implant (10) so as to provide a fully articulating and functional patello-femoral joint replacement device.

In the manufacture of the instruments and devices of the system described herein, the components can be integrally formed or separately formed and assembled using permanent or temporary connections as are well known in the art.

In the preferred embodiment, the implant components would be manufactured from implantable grades of ultra-high molecular weight polyethylene and cobalt chromium molybdenum alloy. The instruments of the system would be manufactured from surgical grade stainless steels. It is within the concept of the present invention that the components may be manufactured from any implantable materials or surgically acceptable materials known in the art, such as, for example titanium alloys, ceramics, composites, or the like.

It is important to recognize that various modifications in the above described configuration and construction of the present invention can be made without departing from the concept of the invention as the specification is only illustrative of the invention, which is limited only by the following claims.

What is claimed is:

1. A patello-femoral joint replacement device shaped to replace only the patella-femoral joint area in a patient in need thereof comprising: a femoral implant component, said femoral implant component having a flat anterior bone facing surface and an upper surface, said upper surface defining an articulating groove disposed along the longitudinal axis of said upper surface, said articulating groove extending uninterrupted from said upper surface to a distally extending projection that terminates at a distal terminus that is configured to have a superior angled upturn.

2. The device of claim 1 further comprising a patellar implant component comprising a securing surface oppositely disposed to an articulating surface, said articulating surface being in a slidable articulation with said articulating groove of said femoral implant, wherein said device has full range of motion of the patello-femoral joint.

3. The device of claim 1, wherein said femoral implant articulating groove has a generally concave configuration longitudinally oriented along said articulating groove and said patellar implant articulating surface has a generally convex configuration that is generally complementary to said articulating groove.

4. The device of claim 2, wherein said securing surface of said patellar implant comprises at least one bone anchor member, sized and configured for insertion into a bone.

5. The device of claim 4, wherein said bone anchor member comprises an annular retaining groove circumferentially disposed around said bone anchor member.

6. The device of claim 4, wherein said patellar securing surface further comprises at least one peg in addition to said bone anchor member.

7. The device of claim 1, wherein said bone facing surface comprises a circumferentially disposed undercut edge along at least a portion of the outer most rim of the femoral implant.

8. The device of claim 1, wherein said bone facing surface comprises at least one recessed pocket sized and configured to receive a portion of adhesive material, said recessed pocket providing additional surface area and improved adhesion when said device is implanted against a bone surface.

9. The device of claim 1, wherein said femoral implant bone facing surface comprises a roughened surface.

10. The device of claim 9, wherein said roughened surface comprises at least one spike or peg.

11. The device of claim 9, wherein said roughened surface comprises a porous coating.

12. The device of claim 1, wherein said femoral implant bone facing surface further comprises an intramedullary stem, said stem being sized and configured for insertion into the femoral canal of a patient, said stem extending substantially parallel to said flat anterior bone facing surface.

13. A patello-femoral joint replacement shaped to replace only the patella-femoral joint area comprising:
a bone facing surface, said bone facing surface having a flat anterior bone facing surface and a distally extending bone facing surface;
a intramedullary stem extending from a distally extending bone facing surface at a first location;
an articulating surface opposite said bone facing surface, said articulating surface defining an articulating groove disposed along a longitudinal axis of said articulating surface, said articulating groove having a concave bearing surface extending continuously between a first upper anterior end to a distal terminus end, said distal terminus end being located beyond said first location, wherein said distal terminus end comprises a superior angled upturn.

14. The patello-femoral joint replacement of claim 13, further comprising a patellar implant having a generally convex articulating surface that is generally complementary to said articulating groove.

15. The patello-femoral joint replacement of claim 13, wherein said flat anterior bone facing surface comprises a circumferentially disposed undercut edge completely around the flat anterior bone facing surface.

16. The patello-femoral joint replacement of claim 13, wherein said bone facing surface comprises at least one recessed pocket; and
adhesive material disposed within the pocket.

17. The patello-femoral joint replacement of claim 13, wherein said femoral implant bone facing surface comprises a roughened surface.

18. The patello-femoral joint replacement of claim 17, wherein said roughened surface comprises at least one fixation spike.

19. A patello-femoral joint replacement shaped to replace only the patello-femoral joint area comprising:
an upper flat anterior bone facing surface having a roughened surface defining a plurality of recessed pockets, said upper flat anterior bone facing surface having a complete circumferentially disposed undercut edge;
a intramedullary stem extending from a distally extending bone facing surface at a first location;
an articulating surface opposite said bone facing surface, said articulating surface defining an articulating groove disposed along a longitudinal axis of said articulating surface, said articulating groove having a concave bearing surface extending continuously between a first upper anterior end to a distal terminus end, said distal terminus being located posterior to said first location, wherein the distal terminus portion of the articulating groove presents a slightly superior angle configured to enable a patellar implant to travel in the articulating groove through the full range of motion of the joint in extremes of flexion.

20. A patello-femoral joint replacement of claim 19, wherein said pockets are disposed anterior to said articulating surface.

21. The patello-femoral joint replacement of claim 19, wherein the upper flat anterior bone facing surface is generally parallel to the stem.

* * * * *